United States Patent
Lim et al.

(10) Patent No.: US 6,660,482 B1
(45) Date of Patent: Dec. 9, 2003

(54) INTER-ALPHA-TRYPSIN INHIBITOR AS A MARKER FOR SEPSIS

(75) Inventors: Yow-Pin Lim, East Providence, RI (US); Douglas C. Hixson, Barrington, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 09/514,450

(22) Filed: Feb. 28, 2000

(51) Int. Cl.$^7$ .................. G01N 33/53; C07K 15/26; C07K 15/28
(52) U.S. Cl. .............. 435/7.1; 530/350; 530/387.1; 530/388.1; 436/500; 436/501
(58) Field of Search .................. 435/7.1; 530/350, 530/387.1, 388.1; 436/500, 501

(56) References Cited

U.S. PATENT DOCUMENTS

| | | | |
|---|---|---|---|
| 5,777,081 A | | 7/1998 | Michalski et al. .......... 530/380 |
| 5,804,370 A | * | 9/1998 | Romaschin et al. .......... 435/5 |

FOREIGN PATENT DOCUMENTS

WO     WO 92/18160     10/1992

OTHER PUBLICATIONS

Piette et al, "Urinary trypsin inhibitory activity for the diagnosis of bacterial infection: a prospective study in 690 patients", Eur. J. Medicine 1(5):273–276, Sep. 1992.*

Byrajalsen et al, "Human inter alpha trypsin inhibitor and immunologically related inhibitors investigated by quantitative immunoelectrophoresis", Clinica Chimica Acta 161:59–68, 1986.*

Trefz et al, "Establishment of an enzyme linked immuno sorbent assay for urinary trypsin inhibitor by using a monoclonal antibody", J. Immunoassay 12(3):347–369, 1991.*

Mizon et al, "Development of an enzyme linked immunosorbent assay for human plasma inter alpha trypsin inhibitor (ITI) using specific antibodies against each of the H1 and H2 heavy chains", J. Immunol. Methods 190:61–70 (1996).*

Daveau et al. (1993) "Human Inter–alpha–inhibitor Family in Inflammation: Simultaneous Synthesis of Positive and Negative Acute–Phase Proteins", *Biochem J*, vol. 292, pp. 485–492.

Michalski et al. (1994) "Preparation and Properties of a Therapeutic Inter–alpha–trypsin Inhibitor Concentrate from Human Plasma", *Vox Sang*, pp. vol. 67, No. 4, pp. 329–336.

Albani, et al. (1997). "Inter–α–Inhibitor as Marker for Neutrophil Proteinase Activity: An In Vitro Investigation" *Journal of Laboratory and Clinical Medicine* 130(3):339–347.

Carrette, et al. (1997). "Pig IαI Appears Unmodified in Plasma in Case of Endotoxin–Induced Disseminated Intravascular Coagulation" *Biochimie* 79(12): 749–755.

* cited by examiner

*Primary Examiner*—Jeffrey Fredman
(74) *Attorney, Agent, or Firm*—Mintz, Levin, Cohn, Ferris, Glovsky & Popeo, P.C.; Ingrid A. Beattie (57) ABSTRACT

The invention provides a method of diagnosing sepsis in a mammal by contacting a bodily fluid from the mammal with a ligand which binds to an inter-alpha trypsin inhibitor (ITI) polypeptide under conditions sufficient to form an ITI-ligand complex and detecting the complex.

20 Claims, 5 Drawing Sheets

SEQUENCE LISTING

<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: Inter-Alpha-Trypsin Inhibitor

<400> SEQUENCE: 1

Ala Val Leu Pro Gln Glu Glu Glu Gly Gly Gly Gly Gly Gln
 1               5                  10

<210> SEQ ID NO 2
<211> LENGTH: 14
<212> TYPE: PRT
<213> ORGANISM: Artificial Sequence -continued

```
<220> FEATURE:
<223> OTHER INFORMATION: Inter-Alpha-Trypsin Inhibitor
<221> NAME/KEY: VARIANT
<222> LOCATION: (6)
<223> OTHER INFORMATION: Wherein X is any of the amino acids.

<400> SEQUENCE: 2

Ser Leu Pro Gly Glu Xaa Glu Glu Met Met Glu Glu Val Asp
 1               5                  10

<210> SEQ ID NO 3
<211> LENGTH: 15
<212> TYPE: PRT
<213> ORGANISM: Artificial Sequence
<220> FEATURE:
<223> OTHER INFORMATION: Inter-Alpha-Trypsin Inhibitor

<400> SEQUENCE: 3

Ser Asx Leu Pro Trp Arg Arg Arg Gly Gly Gly Gly Gly Gln Leu
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Inter-Alpha-Trypsin Inhibitor
<221> NAME/KEY: VARIANT
<222> LOCATION: (6)
<223> OTHER INFORMATION: Wherein X is any amino acid.

<400> SEQUENCE: 4

Ser Leu Pro Gly Glu Xaa Glu Glu Met Met Glu Glu Val Asp Gln
 1               5                  10                  15

<210> SEQ ID NO 5
<211> LENGTH: 352
<212> TYPE: PRT
<213> ORGANISM: Homo sapiens

<400> SEQUENCE: 5

Met Arg Ser Leu Gly Ala Leu Leu Leu Leu Ser Ala Cys Leu Ala
 1               5                  10                  15

Val Ser Ala Gly Pro Val Pro Thr Pro Pro Asp Asn Ile Gln Val Gln
                20                  25                  30

Glu Asn Phe Asn Ile Ser Arg Ile Tyr Gly Lys Trp Tyr Asn Leu Ala
            35                  40                  45

Ile Gly Ser Thr Cys Pro Trp Leu Lys Lys Ile Met Asp Arg Met Thr
        50                  55                  60

Val Ser Thr Leu Val Leu Gly Glu Gly Ala Thr Glu Ala Glu Ile Ser
 65                 70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
        115                 120                 125

Glu Tyr Ala Ile Phe Leu Thr Lys Lys Phe Ser Arg His His Gly Pro
    130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
```

-continued

```
                165               170                  175
Asp Ser Ile Phe Thr Met Ala Asp Arg Gly Glu Cys Val Pro Gly Glu
            180              185                 190

Gln Glu Pro Glu Pro Ile Leu Ile Pro Arg Val Arg Arg Ala Val Leu
        195              200             205

Pro Gln Glu Glu Glu Gly Ser Gly Gly Gly Gln Leu Val Thr Glu Val
    210              215              220

Thr Lys Lys Glu Asp Ser Cys Gln Leu Gly Tyr Ser Ala Gly Pro Cys
225             230              235                     240

Met Gly Met Thr Ser Arg Tyr Phe Tyr Asn Gly Thr Ser Met Ala Cys
            245             250             255

Glu Thr Phe Gln Tyr Gly Gly Cys Met Gly Asn Gly Asn Asn Phe Val
            260             265             270

Thr Glu Lys Glu Cys Leu Gln Thr Cys Arg Thr Val Ala Ala Cys Asn
        275             280             285

Leu Pro Ile Val Arg Gly Pro Cys Arg Ala Phe Ile Gln Leu Trp Ala
    290             295             300

Phe Asp Ala Val Lys Gly Lys Cys Val Leu Phe Pro Tyr Gly Gly Cys
305             310             315                     320

Gln Gly Asn Gly Asn Lys Phe Tyr Ser Glu Lys Glu Cys Arg Glu Tyr
            325             330             335

Cys Gly Val Pro Gly Asp Gly Asp Glu Glu Leu Leu Arg Phe Ser Asn
            340             345             350
```

INTER-ALPHA-TRYPSIN INHIBITOR AS A MARKER FOR SEPSIS

TECHNICAL FIELD

This invention relates to bacterial infections.

BACKGROUND

Sepsis is a systemic response to infection, e.g., a bacterial infection. It is commonly caused by endotoxins from Gram negative bacteria or exotoxins from Gram positive bacteria (which can trigger endotoxin-like responses). The systemic response can lead to septic shock, which is is characterized by a precipitous drop in blood pressure, cardiovascular collapse, and/or multiple organ failure. The mortality rate among patients diagnosed with septic shock can be as high as 35–45%. Rapidly and reliably detecting sepsis has been difficult using conventional diagnostic tools

SUMMARY

The invention provides a method of diagnosing sepsis in a mammal. The methods are also useful as a prognostic tool in predicting the outcome of those diagnosed with sepsis and those undergoing therapy for sepsis.

A method for diagnosis or prognosis sepsis in a mammal is carried out by contacting a bodily fluid, e.g., blood, plasma, or serum, from the mammal with a ligand which binds to an inter-alpha trypsin inhibitor (ITI) polypeptide under conditions sufficient to form an ITI-ligand complex and detecting the complex. The mammal is preferably a human patient; however, the assays are also applicable to veterinary use, e.g., to diagnose or prognose sepsis in animals such as dogs, cats, horses, cows and the like. Preferably, the ligand binds to an epitope of human ITI light chain. ITI is used as a marker for diagnosis or prognosis of sepsis in infants such as neonates as well as adult mammals.

A decrease in the level of ITI in a test sample compared to a normal level of ITI indicates a diagnosis of sepsis. A level of ITI that is at least 10%, more preferably at least 25%, more preferably at least 35% and most preferably at least 50% lower than the a normal level of ITI indicates a diagnosis of sepsis. For example, a normal level of ITI is approximately 1.2 mg/ml of ITI in plasma, and a level of 0.6 mg/ml ITI (or lower) is diagnostic of sepsis. For prognostic purposes, a level of ITI that is at least 10%, more preferably at least 25%, more preferably at least 35% and most preferably at least 50% lower than a diagnostic level of ITI indicates a high risk of mortality (i.e., a poor prognosis). For example, a diagnostic level of ITI is 0.6 mg/ml in plasma, and a level of 0.3 mg/ml ITI (or lower) is predictive of a poor outcome, e.g., septic shock and/or death.

The ITI-ligand used in the method is one that forms a detectable complex with ITI in a bodily fluid. For example, the ligand is an antibody or ITI-binding antibody fragment, e.g., a Fab or (Fab)$_2$ fragment; an engineered single chain Fv molecule; or a chimeric molecule such as an antibody which contains the binding specificity of one antibody, e.g., of murine origin, and the remaining portions of another antibody, e.g., of human origin. Preferably, the antibody is a monoclonal antibody (mAb) such as mAb 69.31. Alternatively, the ligand is a synthetic or proteolytically-generated peptide that binds to an ITI light chain. For detection purposes, the ligand, e.g., ITI-specific antibody, is directly or indirectly labelled using, e.g., a colorimetric or radioisotopic marker. The amount of an immune complex (which contains ITI antigen bound to ITI-specific antibody) is quantitated to determine the level of ITI in the fluid, and the level of ITI in the fluid is compared to a normal control level of ITI (e.g., a previously determined baseline value or the level of ITI from a subject known to be healthy). The claimed assays accurately and reliably diagnose sepsis rapidly (in less time than results are obtained from a conventional bacteremia or sepsis workup).

Prognosis of sepsis is also determined by measuring ITI over time. For example, the method includes the steps of (a) contacting a bodily fluid from a mammal with a ligand which binds to an ITI polypeptide under conditions sufficient to form an ITI-ligand complex and detecting the complex; (b) quantitating the amount of complex to determine the level of ITI in the fluid; and (c) comparing the level of ITI in the fluid over time, wherein a decrease in the concentration of ITI in test samples taken over time indicates an adverse prognosis. Changes in the severity of the sepsis are monitored by comparing changes in the level of ITI in bodily fluids of the patient over time. Such temporal data is used to determine a course of treatment for the patient.

Reagents, e.g., an ITI-specific antibody such as mAb 69.31, for carrying out the diagnostic or prognostic assay may be packaged together as a kit. A kit for diagnosis or prognosis of sepsis in a mammal contains a ligand, e.g., an antibody or antibody fragment, which binds to an ITI light chain and a means of detecting a complex containing the ligand bound to an ITI light chain. The means of detection is preferably a colorimetric marker or radioisotopic marker. For example, the antibody is immobilized on a solid phase and packaged together with other reagents suitable for detecting ITI-ligand complexes. Enzyme-conjugated reagents may be included in the kit. In some embodiments, the antibody or ITI ligand is immobilized on a solid phase such as an assay plate, an assay well, a nitrocellulose membrane, a bead, a dipstick, or a component of an elution column. The immobilized antibody acts as a capture antibody, and a secondary antibody is used to detect the immune complex (e.g., an ITI antigen bound to the mAb 69.31 antibody). The kit may optionally contain a purified ITI polypeptide or purified ITI complex as a control. The polypeptide or complex is purified from natural sources or recombinantly produced. The kit may also contain a second antibody or other detectable marker as described above. For example, the second antibody or marker is labelled, e.g., using a radioisotope, fluorochrome, or other means of detection.

Methods of treating sepsis or reducing the risk of mortality associated with sepsis are also within the invention. A method of treating sepsis in a mammal includes the steps of identifying a mammal suffering from or at risk of developing sepsis and administering to the mammal an ITI composition. The ITI compositions contain an ITI light chain polypeptide or a complex of an ITI light chain polypeptide and an ITI heavy chain polypeptide.

Alternatively, an ITI composition contains a nucleic acid encoding an ITI polypeptide, e.g., a a synthetic oligonucleotide encoding an ITI polypeptide. The ITI composition is preferably administered intravenously.

Other features, objects, and advantages of the invention will be apparent from the description and drawings, and from the claims.

DESCRIPTION OF DRAWINGS

FIG. 2 shows plasma ITI levels in healthy patients compared to patients with sepsis, and FIG. 2 also shows plasma ITI levels in survivors compared to non-survivors of sepsis.

FIG. 4B shows the results of a followup study of patient ITI levels over time.

DETAILED DESCRIPTION

Rapid and reliable detection of sepsis is critical to timely intervention to prevent septic shock and death. The methods described herein are used to detect ITI in bodily fluids of individuals suspected of having or at risk of developing sepsis. Such individuals include those with an infection in the genitourinary tract, the liver or biliary (liver secretion) tract, the gastrointestinal tract, and the lungs. Hospitalized individuals are also at risk of developing sepsis. For example, nocosomial infections which may originate at the site of an intravenous line, surgical wound, surgical drain, or sites of skin breakdown, e.g., a skin ulcer or bedsore, can lead to sepsis. Elderly patients and immunocompromised patients are particularly at risk.

Risk factors associated with sepsis include recent bacterial pneumonia, meningitis, a urinary tract infection that does not respond to antibiotics, osteomyelitis, bacterial peritonitis, a recent dental procedure, a recent endoscopy procedure, a recent cardiovascular procedure, an indwelling urinary catheter, a recent major surgery, cellulites, or a recent therapy with antibiotics.

ITI is a diagnostic and prognostic marker for sepsis Human ITI is a complex glycoprotein normally found in plasma at a relatively high concentration (ca. 0.8 mg/ml). It consists of one light and two heavy polypeptide chains covalently linked by a glycoaminoglycan bond. The light chain, called bikunin, inhibits various serine proteases involved in coagulation and inflammatory networks such as elastase, plasmin, and cathepsin G. Upon activation by serine proteases, bikunin is cleaved from the ITI complex and rapidly excreted by the kidneys. Using a specific monoclonal antibody against human ITI, e.g., mAb 69.31, a competitive ELISA assay was developed. The assay is used to quantitatively measure levels of human ITI in bodily fluids.

Blood samples from 25 septic patients were collected and plasma was separated for determining ITI levels. The results indicate that plasma levels of ITI of sepsis patients were decreased by 20–90% relative to plasma levels of ITI in healthy volunteers. The magnitude of the decrease in plasma ITI levels correlated with the mortality of the patients. Patients with severely decreased levels of ITI (plasma concentration <0.3 mg/ml) demonstrated a higher mortality rate. The mean±SD ITI level was significantly lower in non-survivors (0.35±0.20 mg/ml) compared to survivors (0.58±0.13 mg/ml). These differences persisted for up to 7 days after onset of a severe sepsis (p<0.05).

The assays described herein are used to diagnose sepsis and as a prognostic marker to identify subpopulation of septic patients who might need more aggressive treatment to reduce the mortality risk associated with sepsis. ITI is administered therapeutically to reduce mortality in sepsis. For example, septic patients with low plasma levels of ITI are given ITI in a replacement therapy regimen to improve clinical outcome.

Therapeutic administration of ITI was evaluated using a polymicrobial sepsis model of cecal ligation and puncture (CLP) in the rat. The results indicated that intravenous administration of ITI at a dose of 30 mg/kg body weight at 1 h after CLP increased the survival rate from 30% in vehicle-treated septic rats to 89% (p<0.05; n=9–10). The results indicate that decreased plasma ITI level is associated with higher mortality in septic patients and administration of ITI reduces sepsis-induced lethality.

Neonatal Sepsis

Diagnosis of adult or neonatal sepsis is typically carried out using standard diagnostic tests for bacteremia, e.g., by drawing neonatal blood, performing a bacterial cell culture and blood cell count. Human neonatal sepsis may be caused by various pathogens, including Group B Streptococci, *E. coli,* Listeria, and viruses.

There are several disadvantages associated with a conventional neonatal sepsis workup. Often the blood volume obtained from an infant is suboptimal for conventional tests (5–10 times less than the blood volume drawn from an adult) and the workup can take up to 3 days. If the mother has been undergoing antibiotic treatment, the baby's bacterial culture can be negative, even if bacteria are present.

To detect sepsis in a human infant patient, a blood sample is obtained from the infant using conventional methods. For neonates, the size of the blood sample drawn is typically 200 $\mu$l. Larger sample are drawn according to standard medical practice, taking into account such factors as the size and age of the infant. A blood sample size less than or greater than 200 $\mu$l can be used. When the mother is known to have clinical risk factors for neonatal sepsis, a blood sample from the infant is obtained for testing shortly after birth. Maternal risk factors include maternal fever, fetal tachycardia, rupture of the amniotic membrane more than 12 hours before delivery, foul smelling amniotic fluid, uterine tenderness, increased white blood cell count, and meconium stained amniotic fluid.

If a maternal risk factor is not known to be present, an infant blood sample is obtained as soon as the infant displays signs of infection. Signs of infant infection are known in the art and include evidence of respiratory distress, apnea, petechiae (microbruises under the skin), irregular heart beat, rapid breathing, tachypnea, bulging anterior fontenelle, low blood sugar, and low core temperature.

The methods described herein are rapid (i.e., results can be obtained in a day, often in hours) and can be carried out on a small amount of patient plasma (less than 4–5 $\mu$l of serum or plasma for multiple tests).

Production of ITI-specific antibodies

A panel of mAbs was generated against two different human plasma-derived Factor VII preparations using a standard subtractive immunization protocol. The mice were first immunized with a non-pasteurized preparation (containing ITI), treated with cyclophosphamide, and then injected with a pasteurized preparation. Following sacrifice of the mice, hybridomas were generated and screened using known methods. One of the antibodies (mAb 69.31) was found to bind to a complex glycoprotein which contains several polypeptide chains. Affinity chromatographic purification of the antigen complex with immobilized mAb 69.31 isolated polypeptide antigens of 250 kDa and 125 kDa in size. The bands (on SDS-PAGE) were identified as ITI by N-terminal amino acid sequence analysis; AVLPQEEEGGGGGQ (SEQ ID NO:1); SLPGEXEEMMEEVD (SEQ ID NO:2); SBLP-WRRRGGGGGQL (SEQ ID NO:3); SLPGEXEEM-MEEVDQ (SEQ ID NO:4). Affinity-purified ITI inhibited serine proteases, such as trypsin, plasmin, and elastase.

ITI found in the serum or plasma of human subjects contains one light chain and two heavy polypeptide chains covalently linked by a chondroitin sulfate chain. The light chain (with an apparent molecular mass of 30 kDa) inhibits several serine proteases such as trypsin, human leukocyte elastase (HLE), plasmin and cathepsin G, which proteases are involved in inflammation, shock, tumor invasion, and formation of metastases. Naturally-occurring and recombinant ITI light chains are purified with ITI mAb such as 69.31. Purified ITI light chains are useful to therapeutically inhibit serine proteases.

Deposit

A hybridoma cell line RI 69.31 which produces mAb 69.31 was deposited with the American Type Culture Collection (ATCC) under the terms of the Budapest Treaty on the International Recognition of the Deposit of Microorganisms for the Purpose of Patent Procedure on Dec. 16, 1999, and bears the Patent Deposit Designation PTA-1066. Applicants' assignee acknowledges its duty to replace the deposit should the depository be unable to furnish a sample when requested due to the condition of the deposit before the end of the term of a patent issued hereon, and its responsibility to notify the ATCC of the issuance of such a patent, at which time the deposit will be made available to the public. Prior to that time, the deposit will be made available to the Commissioner of Patents under the terms of CFR §1.14 and 35 U.S.C. §112.

Binding specificity of ITI-specific antibodies

MAb 69.31 was reactive with the light chain of ITI. ITI was purified from human serum by using mAb 69.31 and treated with 0, 1, 5, and 10 g hyaluronidase to cleave the heavy and light chains of ITI. The samples were separated on 12.5% SDS-PAGE and transferred onto nitrocellulose membrane for analysis by Western blot. Without hyaluronidase, two major bands (250 kDa and 125 kDa) were detected with mAb 69.31. With increasing amounts of hyaluronidase, an additional lower molecular weight band (approximately 25–30 kDa) was detected by the antibody. This lower band represented the light chain of ITI. The light and heavy chains of ITI are linked by glycoaminoglycan. Hyaluronidase cleaved the glycoaminoglycan (chondroitin sulfate) chain linking the heavy chain and light chains of the ITI complex, releasing the two chains. These results indicate that mAb 69.31 binds to an epitope located in the light chain of ITI.

The addition of mAb 69.31 to ITI blocked the serine protease inhibitory activity of ITI (as demonstrated by the observed reduction in ITI's inhibition of trypsin activity in the presence of the antibody). These data indicate that the epitope of mAb 69.31 is located in or proximal to the active site of the ITI molecule, i.e., when the 69.31 antibody binds to an ITI light chain molecule, the molecule cannot bind to its substrate. Alternatively, antibody binding alters the 3-dimensional confirmation of ITI, thereby decreasing its serine protease inhibitory activity. Other monoclonal antibodies with the binding specificity of mAb 69.31 are produced and identified using methods known in the art, e.g., competitive binding assays. For example, the active site of ITI light chain contains residues 20–32, residues 241—242, or residues 297–298 of SEQ ID NO:5 (Table 1).

Table 1: Amino Acid Sequence of Human ITI Light Chain

MRSLGALLLL LSACLAVSAG PVPTPPDNIQ VQEN-FNISRI YGKWYNLAIG STCPWLKKIM 61 DRMTVSTLVL GEGATEAEIS MTSTRWRKGV CEETS-GAYEK TDTDGKFLYH KSKWNITES 121 YVVHTNY-DEY AIFLTKKFSR HHGPTITAKL YGRAPQLRET LLQDFRVVAQ GVGIPEDSIF 181 TMADRGECVP GEQEPEPILI PRVRRAVLPQ EEEGSGGGQL VTEVT-KKEDS CQLGYSAGPC 241 MGMTSRYFYN GTS-MACETFQ YGGCMGNGNN FVTEKECLQT CRTVAACNLP IVRGPCRAFI 301 QLWAFDAVKG KCV-LFPYGGC QGNGNKFYSE KECREYCGVP GDGDEELLRF SN (SEQ ID NO:5; residues 1–19=signal peptide)

Diagnostic/Prognostic Assays and Kits

The data described herein demonstrated that significantly lower levels of ITI were detected in plasma or serum of patients with sepsis in contrast to those without sepsis. While Western blot assays offer high specificity in detecting ITI, a quantitative assay such as ELISA is preferred to quantify the levels of ITI in bodily fluids. A normal value range of ITI levels in normal individuals (e.g., healthy volunteers) was determined as a baseline.

Collection of normal baseline data is carried out using conventional analytical techniques and well-known methods of statistical analysis. A "normal level" of ITI means the mean level of ITI in a given bodily fluid for a population of non-septic individuals. A normal range is a mean level among a population of non-septic individuals, plus or minus 10% of the mean, or plus or minus two standard deviations from the mean. Normal ranges are preferably age-matched, i.e., the normal range of ITI levels for a neonate is the mean level of non-septic neonates, and the normal range for an adult is the mean level for non-septic adults.

A standard competitive ELISA format using affinity purified human ITI and Mab 69.31 is used to quantify patient ITI levels. Alternatively, a sandwich ELISA using a capture antibody (Mab 69.31) and a second enzyme-labeled rabbit polyclonal antibody against ITI as a detection antibody is used.

Methods of detecting level of ITI in bodily fluids include contacting a component of a bodily fluid with an ITI-specific antibody bound to solid matrix, e.g., microtiter plate, bead, dipstick. For example, the solid matrix is dipped into a patient-derived sample of a bodily fluid, washed, and the solid matrix contacted with a reagent to detect the presence of immune complexes present on the solid matrix.

Proteins in a test sample are immobilized on (bound to) a solid matrix. Methods and means for covalently or noncovalently binding proteins to solid matrices are known in the art. The nature of the solid surface may vary depending upon the assay format. For assays carried out in microtiter wells, the solid surface is the wall of the well or cup. For assays using beads, the solid surface is the surface of the bead. In assays using a dipstick (i.e., a solid body made from a porous or fibrous material such as fabric or paper) the surface is the surface of the material from which the dipstick is made. Examples of useful solid supports include nitrocellulose (e.g., in membrane or microtiter well form), polyvinyl chloride (e.g., in sheets or microtiter wells), polystyrene latex (e.g., in beads or microtiter plates), polyvinylidine fluoride (known as IMMULON™), diazotized paper, nylon membranes, activated beads, and Protein A beads. Microtiter plates may be activated (e.g., chemically treated or coated) to covalently bind proteins. The solid support containing the antibody is typically washed after contacting it with the test sample, and prior to detection of bound immune complexes.

A common feature of all of these assays is that an ITI-specific antibody is contacted with a sample of bodily fluid under conditions that permit ITI to bind to the antibody forming an immune complex containing the patient ITI bound to an ITI-specific antibody. Such conditions are typically physiologic temperature, pH, and ionic strength. The incubation of the antibody with the test sample is followed by detection of immune complexes by a detectable label. For example, the label is enzymatic, fluorescent, chemiluminescent, radioactive, or a dye. Assays which amplify the signals from the immune complex are also known in the art, e.g., assays which utilize biotin and avidin.

An ITI-detection reagent, e.g., an antibody, is packaged in the form of a kit. The kit may contain in separate containers an antibody (either already bound to a solid matrix or packaged separately with reagents for binding them to the matrix), control formulations (positive and/or negative), and/or a detectable label. Instructions (e.g., written, tape, VCR, CD ROM, etc.) for carrying out the assay may be included in the kit. The assay may be in the form of a standard sandwich ELISA format known in the art.

For example, an ITI capture antibody, e.g., mAb 69.31, is immobilized on a solid matrix such as a porous strip to form at least one ITI detection site. The measurement or detection region of the porous strip may include a plurality of sites containing an immobilized antibody. A test strip may also contain sites for negative and/or positive controls. Alternatively, control sites are located on a separate strip from the test strip. Optionally, the different detection sites may contain different amounts of immobilized antibody, i.e., a higher amount in the first detection site and lesser amounts in subsequent sites. For example, if 20 nanograms of antibody captures the equivalent of 1 nmol/min/ml of ITI, then the first detection site of an assay device might contain 50 nanograms of the antibody while the subsequent sites contain 10, 20, 30, etc. nanograms of antibody. Upon the addition of test sample, the number of sites displaying a detectable signal provides a quantitative indication of the amount of ITI present in the sample. The detection sites may be configured in any suitably detectable shape and are typically in the shape of a bar spanning the width of a teststrip.

A multi-capture assay configuration is prepared such that if a threshold amount of ITI is not present in the test sample, then substantially all of the ITI will bind to the antibody in the first capture site and thus become immobilized at that site. If a greater than threshold amount of ITI is present in the test sample, the remaining ITI binds to subsequent detection zones of immobilized antibody along the length of the teststrip. The greater the amount of ITI in the test sample, the greater the number of capture sites that will display a detectable signal due to the presence of ITI.

Therapeutic Administration of ITI

ITI is administered to treat sepsis, prevent the development of sepsis, or reduce mortality associated with sepsis. An ITI polypeptide or DNA encoding an ITI polypeptide is administered to increase the level of ITI in patients with severe bacterial infections or with previously diagnosed sepsis. ITI polypeptides are administered to the patient using conventional methods in a pharmaceutically acceptable carrier such as physiological saline using standard methods. ITI is administered to elevate plasma serum levels, e.g., to bring levels into a normal range of ITI concentration. In the rat model described below, 30 mg/kg of ITI was administered in a single dose. Doses for human patients are extrapolated from animal models using methods known in the art. It is expected that an intravenous dosage of approximately 1 to 100 moles of the polypeptide of the invention would be administered per kg of body weight per day. The compositions of the invention are useful for parenteral administration, such as intravenous, subcutaneous, intramuscular, and intraperitoneal.

A therapeutic ITI polypeptide has an amino acid sequence that is at least 50% identical to a naturally-occurring ITI amino acid sequence, e.g., SEQ ID NO:5. More preferably, the sequence is at least 75% identical, more preferably 85% identical, more preferably 95% identical, more preferably 99% identical, and most preferably 100% identical to a naturally-occurring ITI sequence.

Nucleotide and amino acid comparisons are carried out using the Lasergene software package (DNASTAR, Inc., Madison, Wis.). The MegAlign module used was the Clustal V method (Higgins et al., 1989, CABIOS 5(2):151–153). The parameter used were gap penalty 10, gap length penalty 10.

ITI fragments to be administered are at least 50% (more preferably 99%, and most preferably 100%) identical to a naturally occurring ITI sequence and have a biological activity of a naturally-occurring ITI polypeptide. For example, a biological activity of ITI is reduction of serine protease activity or inhibition of metastasis or invasiveness of cancer cells, e.g., as measured in the 3-D cell invasion assay described herein. The therapeutic polypeptide preferably contains residues 20–32, residues 241–242, or residues 297–298 of SEQ ID NO:5 (Table 1). The polypeptide preferably contains residue 215 which participates in binding to ITI heavy chain via chondroitin sulfate.

An ITI polypeptide for therapeutic administration is substantially pure. Preferably, the ITI polypeptide is the mature form of the polypeptide, i.e., it lacks the signal peptide. Polypeptides are "substantially pure" when they are within preparations that are at least 60% by weight (dry weight) the compound of interest. Preferably, the preparation is at least 75%, more preferably at least 90%, and most preferably at least 99%, by weight the compound of interest. Purity is measured by any appropriate standard method, e.g., by column chromatography, polyacrylamide gel electrophoresis, or HPLC analysis.

To render the therapeutic peptides less susceptible to cleavage by peptidases, the peptide bonds of a peptide may be replaced with an alternative type of covalent bond (a "peptide mimetic"). Where proteolytic degradation of the peptides following injection into the subject is a problem, replacement of a particularly sensitive peptide bond with a noncleavable peptide mimetic will make the resulting peptide more stable and thus, more useful as a therapeutic. Such mimetics, and methods of incorporating them into polypeptides, are well known in the art. Similarly, the replacement of an L-amino acid residue with a D-amino acid is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

DNA encoding ITI polypeptides is introduced into target cells of the patient by standard vectors and/or gene delivery systems. Suitable gene delivery systems include liposomes, receptor-mediated delivery systems, naked DNA, and viral vectors such as herpes viruses, retroviruses, and adenoviruses, among others.

EXAMPLE 1
Plasma Levels of ITI as a Marker for Sepsis

Figure 1:
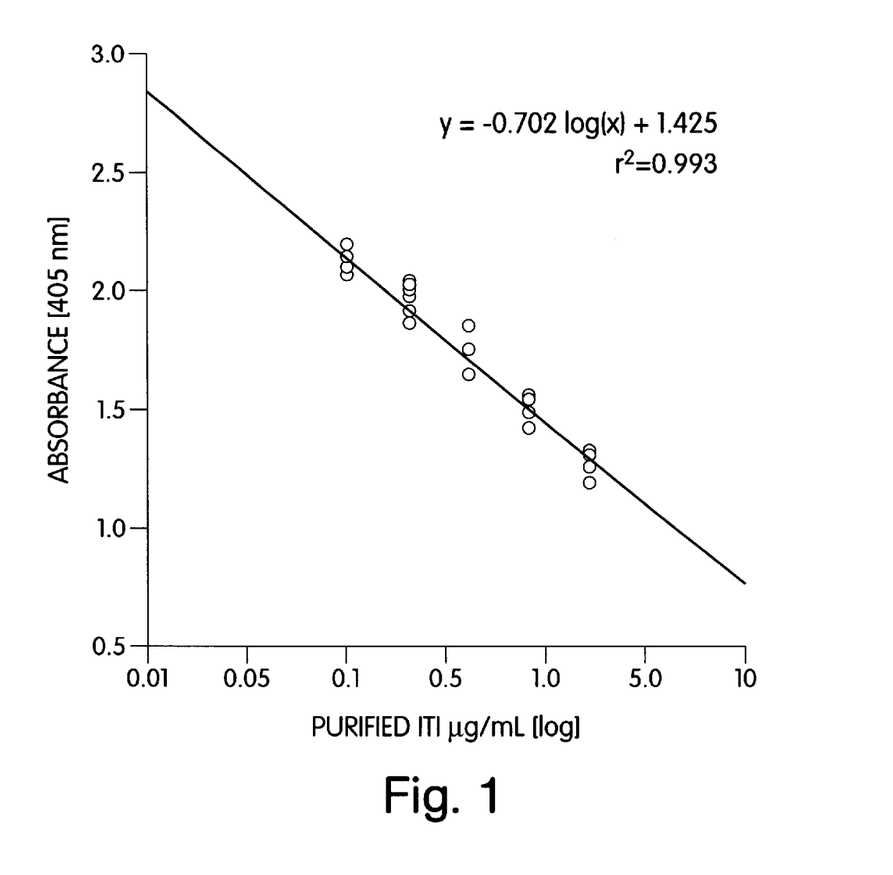
FIG. 1 is a FIG. 1 is a line graph showing the specificity of binding of mAb 69.31 using a competitive ELISA assay.

Plasma levels of ITI in healthy individuals and septic patients were measured by a competitive ELISA using a monoclonal antibody specific which binds to human ITI (e.g., MAb 69.31). A standard curve of the immunoassay was established by using serially diluted of known amount of purified ITI (FIG. 1). The assay was used to reliably and accurately measure the levels of ITI in plasma in a range between 0.1–2.5 µg/mL. To determine the ITI level in a test plasma or serum sample, the sample was diluted 1:1000 to 1:2500 in PBS and the concentration of ITI calculated based on the standard curve.

Figure 2A:
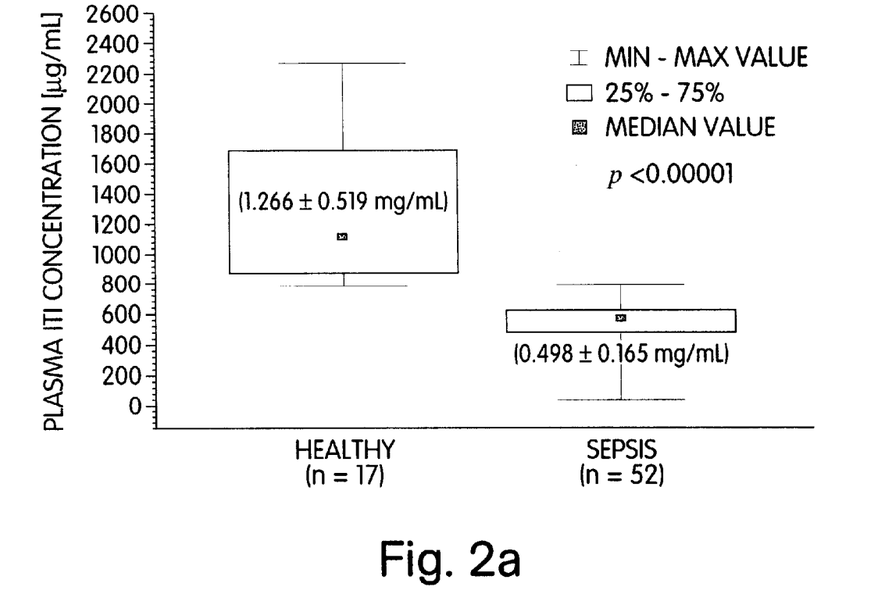
FIG. 2 are line graphs showing the range of ITI levels in plasma of human patients.
Figure 2B:
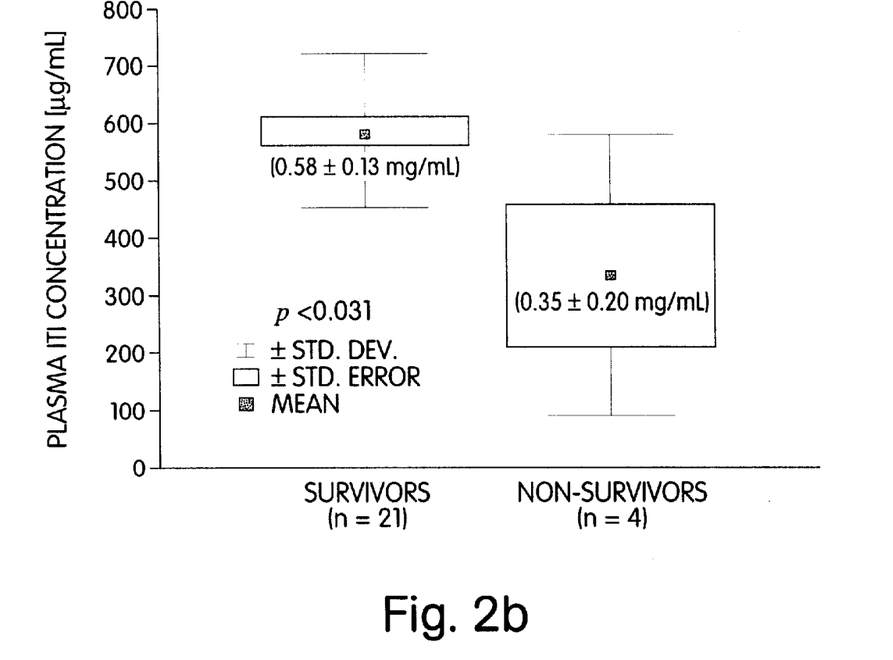

Plasma levels of ITI were determined in healthy individuals, individuals known to have sepsis (as determined by conventional clinical parameters), survivors of sepsis, and nonsurvivors of sepsis. Using the competitive ELISA, plasma ITI levels from a group of healthy individuals (n=17) were compared to the levels of septic patients (n=52). The results (FIG. 2) indicated that the mean of ITI levels of healthy individuals was significantly higher compared to the mean of septic patient group (1.266±0.519 mg/ml compared to 0.498±0.165 mg/ml). The difference is statistically significant (p=<0.0001).

Figure 3:
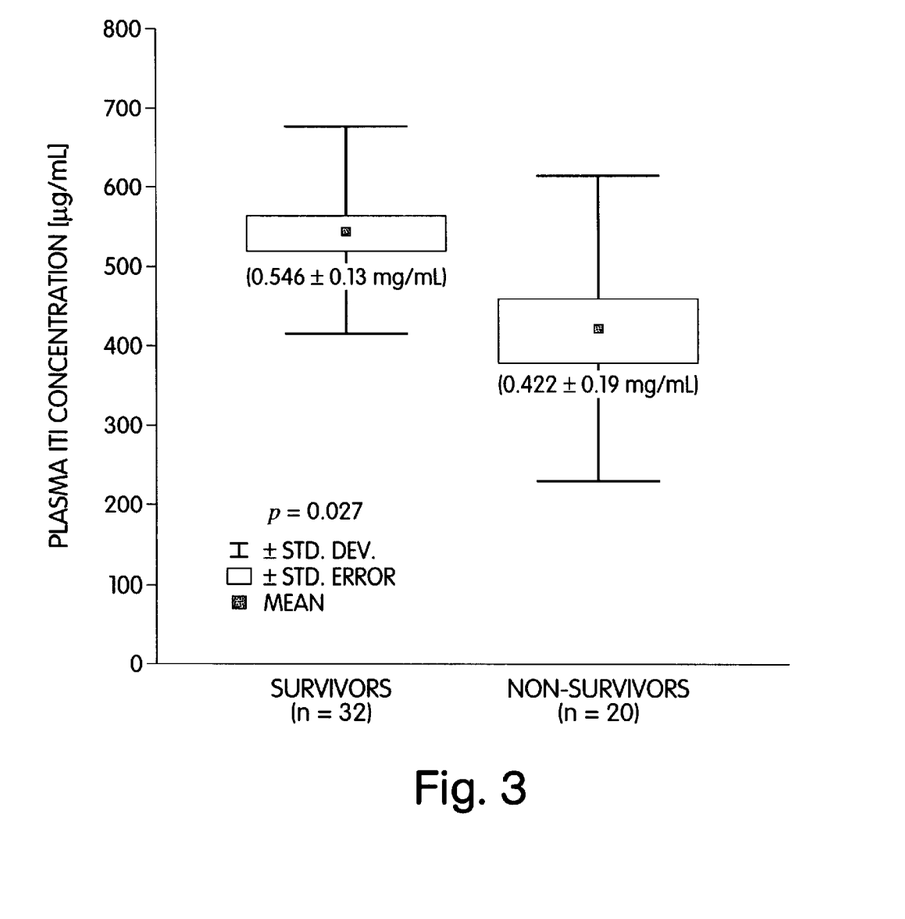
FIG. 3 is a line graph showing the range of ITI levels in plasma of human patients in an expanded population of patients. The levels detected in survivors compared to non-survivors of sepsis confirm the data shown in FIG. 2B.

When 25 plasma samples from septic patients were further analyzed based on the outcome, the group of survivors demonstrated higher levels of ITI compared to the patients who did not survive sepsis (non-survivors). The mean ITI levels were 0.58±0.13 mg/ml compared to 0.35±0.20 mg/ml, respectively. The difference between the ITI levels of each group was statistically significant (p=0.031). The results indicate that a decreased level of ITI (compared to a normal, non-septic level) correlates with increased septic mortality. The results shown in FIG. 2 were further confirmed in a larger septic patient study involving 32 survivors and 20 non-survivors. The results (FIG. 3) were consistent with the data shown in FIG. 2.

EXAMPLE 2
Plasma ITI Levels are Prognostic of Mortality

Figure 4A:
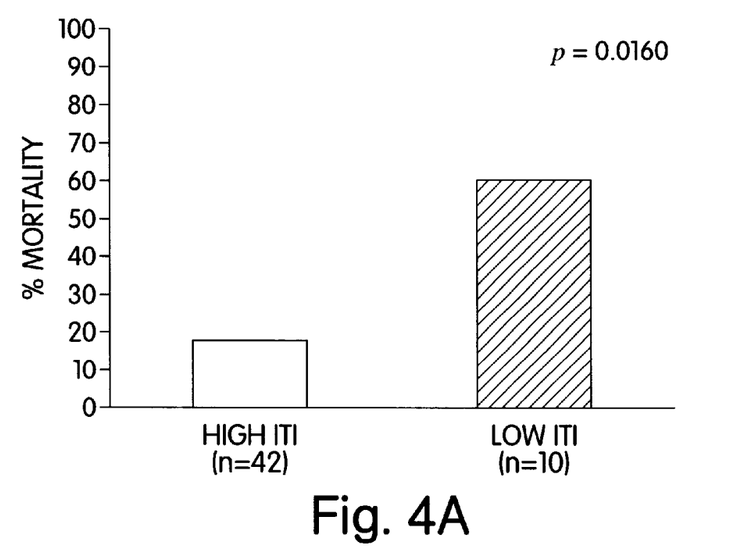
FIGS. 4A–B are bar graphs showing the correlation between plasma ITI level and mortality. The data plotted in FIG. 4A shows that patients with low plasma ITI levels had a higher mortality rate compared to those with high plasma ITI levels.
Figure 4B:
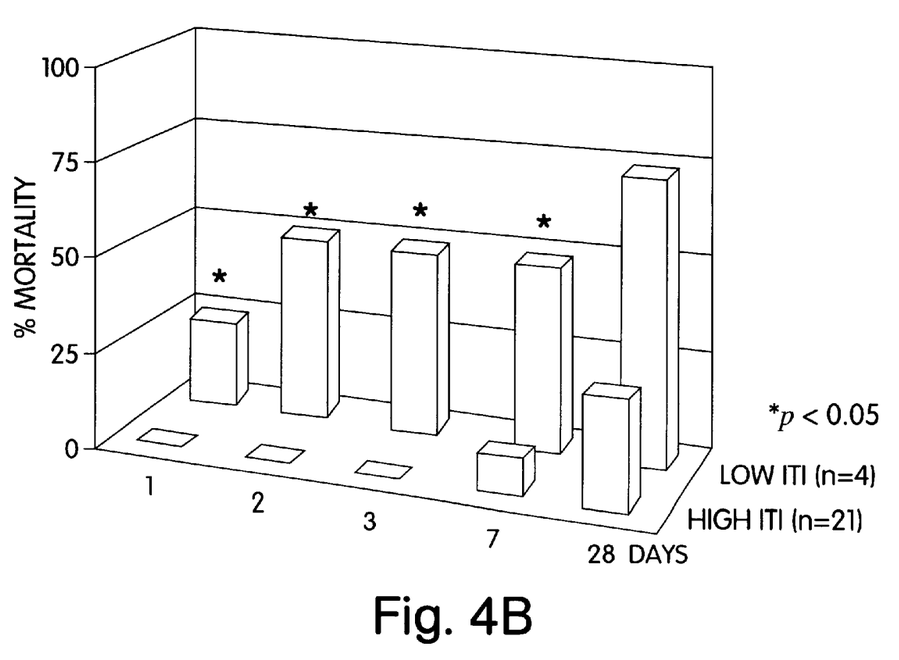
Figure 5:
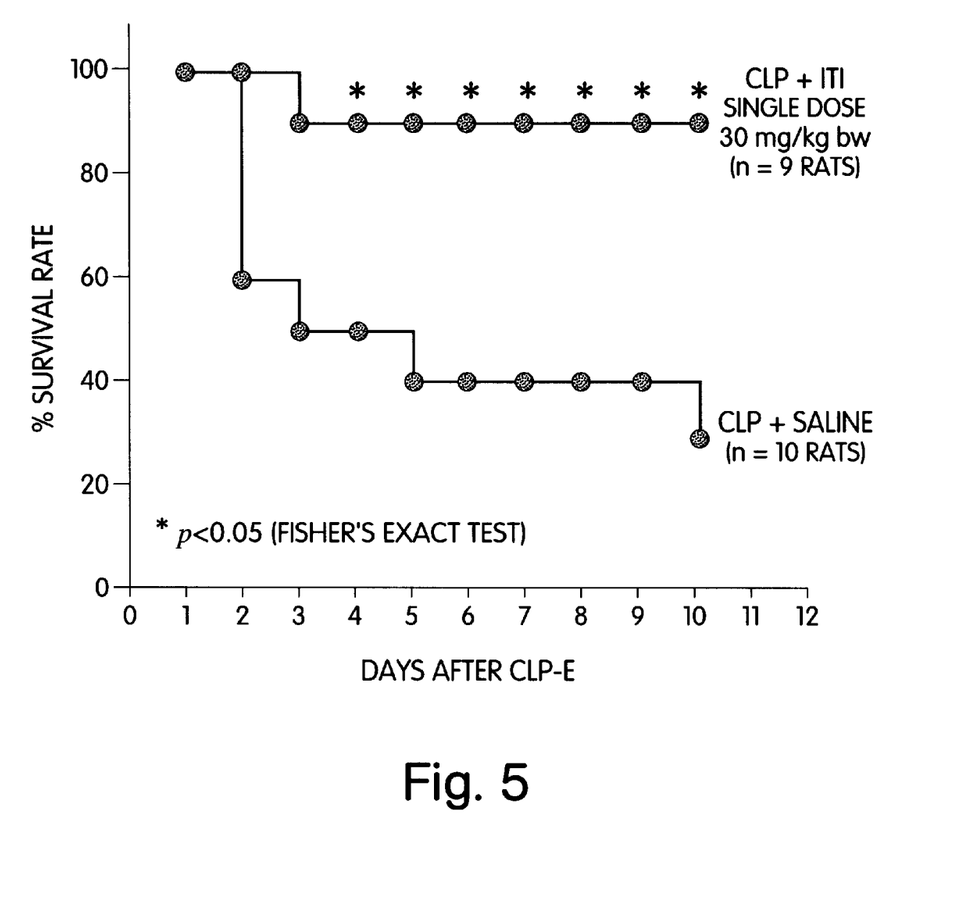
FIG. 5 is a line graph showing the effect of ITI on the mortality rate after CLP and caecal excision

The correlation between low ITI plasma levels and mortality rate is shown in FIGS. 4A–B. Sixty per cent (6 out of 10) of septic patients who died demonstrated severely decreased levels of ITI in the plasma (<0.3 mg/ml). In contrast, elevated levels of ITI were detected in 19% (8 out of 42) of septic patients who died (ITI levels >0.30 mg/ml). The difference was statistically significant at p=0.016.

When patients were followed over time, patients with low levels of ITI demonstrated a higher mortality rate than patients with high levels of ITI (FIG. 4B) These differences persisted for up to 7 days after onset of a severe sepsis (p<0.05).

These data indicate that serum or plasma ITI levels are useful to determine the prognosis of patients with infection (e.g., individuals at risk of developing sepsis or those who are undergoing treatment for sepsis). For example, in addition to use as a diagnostic and prognostic tool for sepsis, the assays described herein are useful to monitor the progress of individuals undergoing a particular treatment regimen (for infection and/or sepsis) and provide a basis for altering a prescribed treatment protocol.

EXAMPLE 3
Therapeutic Administration of ITI Reduced Mortality from Sepsis Effect of ITI-based therapy on mortality rate was evaluated using an art-recognized in-vivo animal model of sepsis. The rat model is a polymicrobial sepsis model of cecal ligation and puncture (CLP) and caecal excision (CLPE). Adult male Sprague-Dawley rats were subjected to sepsis by CLP and CLPE using standard methods. Purified ITI (30 mg/kg body weight in 1 mL saline) was perfused intravenously for 30 min, starting at 1 hour after the onset of CLP. Control rats received only saline instead of ITI. At 20 hr. after CLP, the necrotic cecum was removed and mortality was monitored for 10 days.

The results indicated that intravenous administration of ITI at a single dose of 30 mg/kg body weight at 1 h after CLP increased the survival rate from 30% in saline control septic rats to 89% (p<0.05; n=9–10). These data indicate that decreased plasma ITI level is associated with higher mortality in septic patients and that administration an ITI composition to individuals suffering from or at risk of developing sepsis confers a clinical benefit, e.g., reduction in sepsis-induced lethality. Administration of a human ITI polypeptide is useful to reduce mortality due to sepsis.

A number of embodiments of the invention have been described. However, modifications to the methods and compositions described herein may be made without departing from the spirit and scope of the invention. Other embodiments are within the scope of the following claims.

---

What is claimed is:

1. A method for diagnosis of sepsis in a mammal, comprising contacting a bodily fluid from said mammal with a monoclonal antibody which binds to bikunin, a bikunin-containing inter-alpha trypsin inhibitor (ITI) glycoprotein with an apparent molecular mass of 250 kDa and a bikunin-containing ITI glycoprotein with an apparent molecular mass of 125 kDa under conditions sufficient to form an immune complex and detecting the immune complex to determine an ITI level, wherein said bodily fluid is blood, serum, or plasma, and wherein a decrease in the level of ITI in a test sample compared to a normal level of ITI indicates a diagnosis of sepsis.

2. The method of claim 1, wherein said mammal is a human.

3. The method of claim 1, wherein said mammal is a human infant.

4. The method of claim 1, wherein said fluid is blood.

5. The method of claim 1, wherein said fluid is plasma.

6. The method of claim 1, wherein said fluid is serum.

7. The method of claim 1, wherein said monoclonal antibody is 69.31.

8. A method for prognosis of sepsis of a mammal, comprising contacting a bodily fluid from said mammal with a monoclonal antibody which binds to an bikunin, a bikunin-containing inter-alpha trypsin inhibitor (ITI) glycoprotein with an apparent molecular mass of 250 kDa, and a bikunin-containing ITI glycoprotein with an apparent molecular mass of 125 kDa under conditions sufficient to form an immune complex;
    quantitating the amount of complex to determine the level of ITI in said fluid; and comparing the level of ITI in said fluid over time, wherein said bodily fluid is blood, serum, or plasma, and wherein decreasing levels of ITI over time indicates an adverse prognosis.

9. The method of claim 8, wherein said bodily fluid is blood.

10. The method of claim 8, wherein said fluid is plasma or serum.

11. The method of claim 8, wherein said monoclonal antibody is 69.31.

12. The method of claim 1, wherein said monoclonal antibody binds to an epitope of human ITI light chain.

13. The method of claim 8, wherein said monoclonal antibody binds to an epitope of human ITI light chain.

14. The method of claim 1, wherein a level of 0.6 mg/ml or lower of ITI glycoprotein in said bodily fluid indicates a diagnosis of sepsis.

15. The method of claim 8, wherein a level of 0.3 mg/ml or lower of said ITI glycoprotein in said bodily fluid indicates a prognosis of septic shock or death.

16. The method of claim 1, wherein said level of ITI glycoprotein is at least 10% lower than said normal level.

17. The method of claim 1, wherein said level of ITI glycoprotein is at least 25% lower than said normal level.

18. The method of claim 1, wherein said level of ITI glycoprotein is at least 35% lower than said normal level.

19. The method of claim 1, wherein said level of ITI glycoprotein is at least 50% lower than said normal level.

20. A method for prognosis of sepsis, comprising contacting a bodily fluid from said mammal with a monoclonal antibody which binds to a bikunin-containing inter-alpha trypsin inhibitor (ITI) glycoprotein with an apparent molecular mass of 250 kDa and a bikunin-containing ITI glycoprotein with an apparent molecular mass of 125 kDa under conditions sufficient to form an immune complex and detecting the immune complex to determine an ITI level, wherein said bodily fluid is blood, serum, or plasma, and wherein an ITI level of 0.3 mg/ml or lower indicates a high risk of mortality.

* * * * *